US00PP35936P2

(12) United States Plant Patent
Tatro

(10) Patent No.: US PP35,936 P2
(45) Date of Patent: Jul. 2, 2024

(54) ***VERBENA* PLANT NAMED 'WNVERSVCB24'**

(50) Latin Name: *Verbena hybrida*
Varietal Denomination: WNVERSVCB24

(71) Applicant: Jessica Tatro, Allenstown, NH (US)

(72) Inventor: Jessica Tatro, Allenstown, NH (US)

(73) Assignee: WINGEN, LLC, Mustang Ridge, TX (US)

( * ) Notice: Subject to any disclaimer, the term of this patent is extended or adjusted under 35 U.S.C. 154(b) by 18 days.

(21) Appl. No.: 18/237,788

(22) Filed: Aug. 24, 2023

(51) Int. Cl.
*A01H 5/02* (2018.01)
*A01H 6/86* (2018.01)

(52) U.S. Cl.
USPC ..... Plt./308

(58) Field of Classification Search
USPC ..... Plt./308
See application file for complete search history.

*Primary Examiner* — Susan McCormick Ewoldt
(74) *Attorney, Agent, or Firm* — C. Anne Whealy

(57) ABSTRACT

A new and distinct cultivar of *Verbena* plant named 'WNVERSVCB24', characterized by its upright to outwardly spreading and mounding to trailing and decumbent plant habit; vigorous growth habit and rapid growth rate; freely branching habit; dark green-colored leaves; freely flowering habit; large inflorescences with purplish pink, purplish red and white-colored flowers that may be solid or multi-colored; flowers that are held above and beyond the foliar plane; and resistance to Powdery Mildew.

2 Drawing Sheets

Figure 1:
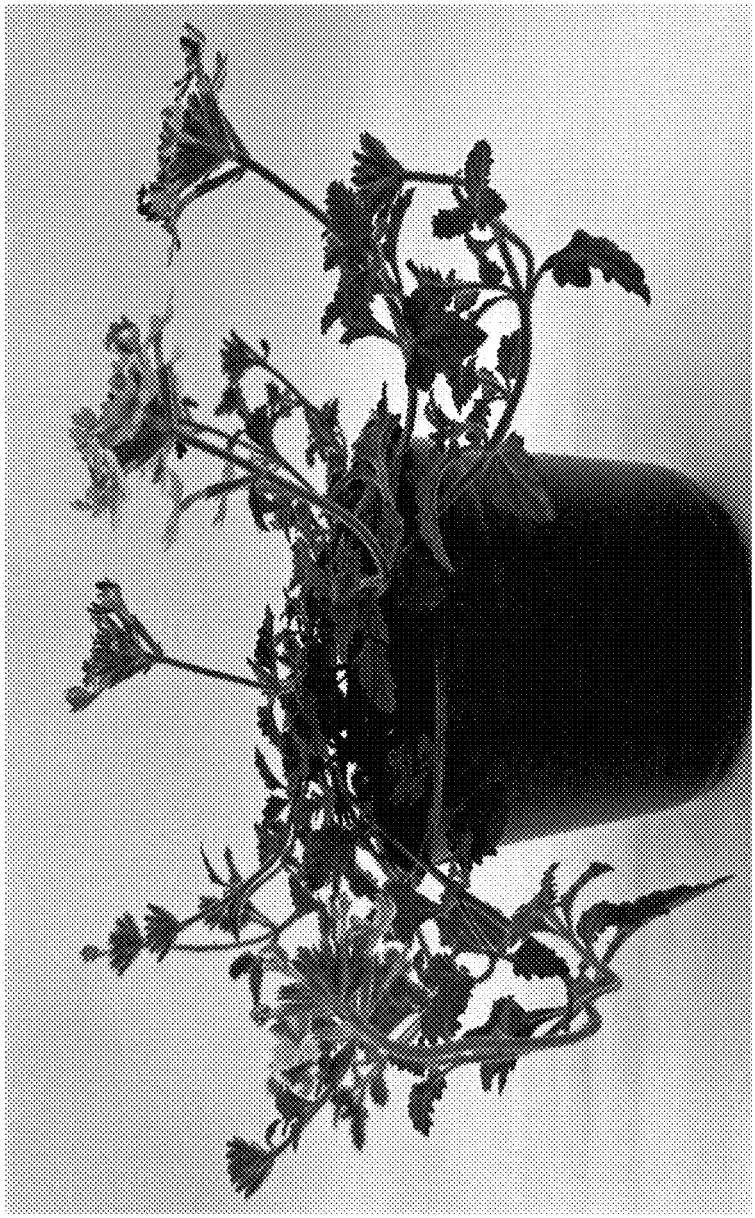

Botanical designation: *Verbena hybrida.*
Cultivar denomination: 'WNVERSVCB24'.

BACKGROUND OF THE INVENTION

The present invention relates to a new and distinct cultivar of *Verbena* plant, botanically known as *Verbena hybrida* and hereinafter referred to by the name 'WNVERSVCB24'.

The new *Verbena* plant is a naturally-occurring branch mutation of *Verbena hybrida* 'RIKAV45801', disclosed in U.S. Plant Pat. No. 30,899. The new *Verbena* plant was discovered and selected by the Inventor on a single flowering plant within a population of plants of 'RIKAV45801' in a controlled greenhouse environment in Loudon, New Hampshire on Dec. 4, 2020.

Asexual reproduction of the new *Verbena* plant by vegetative terminal cuttings in a controlled environment in Loudon, New Hampshire since Dec. 20, 2020, has shown that the unique features of this new *Verbena* plant are stable and reproduced true to type in successive generations.

SUMMARY OF THE INVENTION

Plants of the new *Verbena* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WNVERSVCB24'. These characteristics in combination distinguish 'WNVERSVCB24' as a new and distinct *Verbena* plant:

1. Upright to outwardly spreading and mounding to trailing and decumbent plant habit.
2. Vigorous growth habit and rapid growth rate.
3. Freely branching habit.

4. Dark green-colored leaves.
5. Freely flowering habit.
6. Large inflorescences with purplish pink, purplish red and white-colored flowers that may be solid or multi-colored.
7. Flowers that are held above and beyond the foliar plane.
8. Resistance to Powdery Mildew (*Podosphaera xanthii*).

Plants of the new *Verbena* can be compared to plants of the mutation parent, 'RIKAV17805', primarily in flower color as plants of the new *Verbena* have purplish pink, purplish red and white-colored flowers that may be solid or multi-colored whereas plants of 'RIKAV17805' have solid dark red purple-colored flowers.

Plants of the new *Verbena* can be compared to plants of the *Verbena hybrida* 'RIKAV18302M', disclosed in U.S. Plant Pat. No. 29,640. In side-by-side comparisons, plants of the new *Verbena* differ primarily from plants of 'RIKAV18302M' in flower color as plants of the new *Verbena* have purplish pink, purplish red and white-colored flowers that may be solid or multi-colored whereas plants of 'RIKAV18302M' have light violet blue and white bi-colored flowers. In addition, flowers of plants of the new *Verbena* are somewhat smaller than flowers of plants of 'RIKAV18302M'.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the colors of the new *Verbena* plant.

The photograph on the first sheet (FIG. 1) is a side perspective view of a typical flowering plant of 'WNVERSVCB24' grown in a container.

Figure 2:
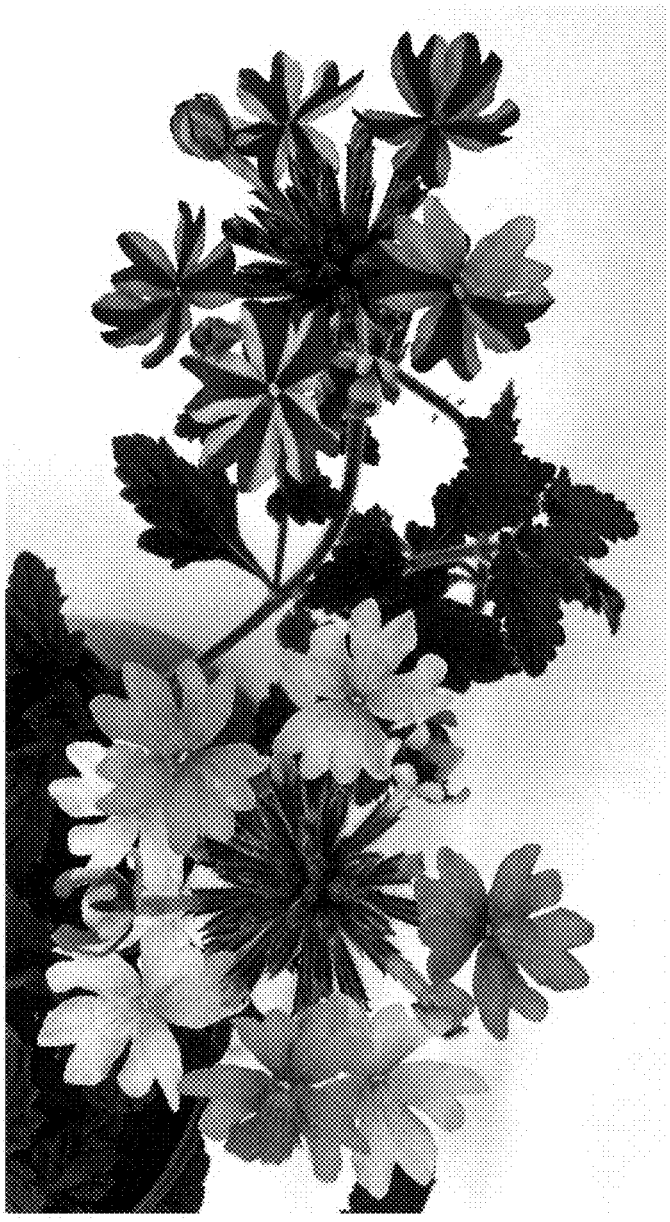

The photograph on the second sheet (FIG. 2) is a close-up view of typical inflorescences of 'WNVERSVCB24'.

DETAILED BOTANICAL DESCRIPTION

The aforementioned photographs and following observations and measurements describe plants grown during the spring in 723 ml containers in a glass-covered greenhouse in Loudon, New Hampshire and under cultural practices typical of commercial *Verbena* production. During the production of the plants, day and night temperatures averaged 20 C. Plants were seven weeks from planting rooted cuttings when the photographs and description were taken. In the following description, color references are made to The Royal Horticultural Society Colour Chart, 2015 Edition, except where general terms of ordinary dictionary significance are used.

Botanical classification: *Verbena hybrida* 'WNVERSVCB24'.

Parentage: Naturally-occurring branch mutation of *Verbena hybrida* 'RIKAV45801', disclosed in U.S. Plant Pat. No. 30,899.

Propagation:

*Type cutting*.—Vegetative terminal cuttings.

*Time to initiate roots, summer*.—About three days at temperatures ranging from about 16 C to 29 C.

*Time to initiate roots, winter*.—About four days at temperatures ranging from about 16 C to 21 C.

*Time to produce a rooted plant, summer*.—About 15 days at temperatures ranging from about 16 C to 29 C.

*Time to produce a rooted plant, winter*.—About 20 days at temperatures ranging from about 16 C to 21 C.

*Root description*.—Medium in thickness, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Upright to outwardly spreading and mounding to trailing and decumbent plant habit; freely branching habit with about five to eight primary lateral branches each with secondary lateral branches potentially developing at every node, pinching enhances branching potential; dense and bushy plant habit; vigorous growth habit and rapid growth rate.

*Plant height*.—About 11 cm.

*Plant diameter* (*spread*).—About 36 cm to 42 cm.

Lateral branch description:

*Length*.—About 31.5 cm.

*Diameter*.—About 2.25 mm.

*Internode length*.—Variable, about 1.7 cm to 3 cm.

*Orientation*.—Initially upright then outwardly spreading to trailing and decumbent.

*Strength*.—Strong; flexible; not brittle.

*Texture and luster*.—Densely pubescent; semi-glossy; becoming woody with subsequent development.

*Color, developing*.—Closest to 146A.

*Color, developed*.—Closest to 146A; if woody, close to 199A.

Leaf description:

*Arrangement*.—Opposite, simple.

*Length*.—About 3.25 cm to 3.5 cm.

*Width*.—About 2.1 cm to 2.25 cm.

*Shape*.—Ovate.

*Apex*.—Acute.

*Base*.—Truncate.

*Margin*.—Deeply crenate; not undulate.

*Texture and luster, upper surface*.—Slightly to moderately pubescent, rough; slightly glossy.

*Texture and luster, lower surface*.—Mostly glabrous with dense pubescence along veins; slightly glossy to matte.

*Venation pattern*.—Pinnate.

*Color*.—Developing leaves, upper surface: Closest to 147A. Developing leaves, lower surface: More green than 147B. Fully expanded leaves, upper surface: Closest to between 147A and 139A; midvein, proximally, closest to between 144A and 146A and distally, closest to between 147A and 139A; lateral venation, closest to between 147A and 139A. Fully expanded leaves, lower surface: More green than 147B; venation, closest to 144A.

*Petioles*.—Length: About 1.2 cm. Diameter: About 2 mm to 2.5 mm. Strength: Strong; flexible. Texture and luster, upper and lower surfaces: Densely pubescent; semi-glossy. Color, upper surface: Closest to 144A; edges, close to between 147A and 139A. Color, lower surface: Closest to 144A; edges, more green than 147A.

Flower description:

*Flower arrangement and habit*.—Sessile salverform flowers arranged in upright hemispherical terminal corymbs; flowers face upward or outwardly depending on the position in the inflorescence; freely flowering habit with about 20 to 24 flowers developing per inflorescence; inflorescences potentially forming at every node and numerous inflorescences developing per plant during the flowering season.

*Natural flowering season*.—Plants flower continuously from spring until the autumn; early flowering habit, plants begin flowering about five to six weeks after planting.

*Flower longevity*.—Flowers last about five to seven days on the plant; flowers may be persistent.

*Fragrance*.—Faint; pleasant.

*Inflorescence height*.—About 2.25 cm.

*Inflorescence diameter*.—About 5.75 cm.

*Inflorescence buds*.—Length: About 1 cm. Diameter: About 1.1 cm. Shape: Somewhat conical. Texture and luster: Pubescent; semi-glossy. Color: Closest to 146A.

*Flower buds*.—Length: About 6 mm. Diameter: About 5 mm. Shape: Ovoid to conical, tubular. Texture and luster: Pubescent; slightly glossy. Color: Closest to 146A.

*Flower diameter*.—About 2 cm.

*Flower depth* (*height*).—About 2 cm to 2.1 cm.

*Throat diameter*.—About 1.5 mm to 2 mm.

*Tube length*.—About 1.8 cm to 1.9 cm.

*Tube diameter, proximally*.—About 1.5 mm to 2 mm.

*Corolla*.—Arrangement: Single whorl of five fused petals fused towards the base into a slender narrow tube. Petal lobe length: About 9 mm. Petal lobe width: About 7.5 mm to 8 mm. Petal lobe shape: Cordate. Petal lobe apex: Deeply and broadly emarginate. Petal margin: Entire; slightly undulate. Petal texture and luster, upper and lower surfaces: Smooth, glabrous; slightly iridescent; matte. Throat texture and luster: Smooth, glabrous; glossy. Tube texture and luster: Smooth, glabrous; slightly glossy. Color: Petal lobes, when opening and fully opened, upper surface, solid-colored lobes: Closest to 62A to 62B or closest to NN155D; venation, similar to lamina color. Petal lobes, when opening and fully opened, upper surface, multi-colored lobes: Centers, closest to N57A and towards the margins, closest to 62A to 62B, 62C to 62D, and/or NN155D; with subsequent development, center closest becoming closer to N57B to N57C and towards the margins, closest to NN155D; venation, similar to lamina colors. Petal lobes, when opening and fully opened, lower surface, solid and multi-color lobes: Centers, closest to 62A and towards the margins, closest to 62D, with colors from upper surface visible; with subsequent development, center color becoming closest to 62B to 62C and towards the margins, closest to 62C to 62D; venation, similar to lamina colors. Throat: Closest to NN155D; venation, close to NN155D. Tube: Close to 157A; venation, close to 157A.

*Calyx*.—Arrangement: Single whorl of five fused sepals fused towards the base into a slender tube. Length: About 1.2 cm. Diameter: About 2 mm. Sepal length: About 1.2 cm. Sepal width: Less than 1 mm. Sepal shape: Linear. Sepal apex: Sharply acute. Sepal margin: Free part, entire. Sepal texture and luster, upper surface: Smooth, glabrous; slightly glossy. Sepal texture and luster, lower surface: Pubescent; slightly glossy. Sepal color, upper surface: Closest to 146A. Sepal color, lower surface: Closest to 147A.

*Peduncles*.—Length: About 4.8 cm to 5.1 cm. Diameter: About 2 mm. Strength: Strong; flexible, wiry. Aspect: Mostly upright. Texture and luster: Densely pubescent; semi-glossy. Color: Closest to 146A.

*Reproductive organs*.—Stamens: Quantity and arrangement: Five per flower, filaments mostly adnate to corolla tube. Filament length: About 1.2 cm. Filament color: Closest to 157A. Anther size: About 0.75 mm by 0.9 mm. Anther shape: Oblong. Anther color: Closest to N144A. Pollen amount: None observed. Pistils: Quantity: One per flower. Pistil length: About 1.75 cm. Stigma shape: Biparted. Stigma diameter: About 0.9 mm. Stigma color: Closest to 144A. Style length: About 1.6 cm. Style color: Closest to 145A. Ovary color: Closest to 144A. Fruits and seeds: To date, fruit and seed development have not been observed on plants of the new *Verbena*.

Temperature tolerance: Plants of the new *Verbena* have been observed to tolerate temperatures from about 2 C to about 40 C and are suitable for USDA Hardiness Zones 8a to 11b.

Pathogen & pest resistance: Plants of the new *Verbena* have been observed to be resistant to Powdery Mildew (*Podosphaera xanthii*). To date, plants of the new *Verbena* have not been observed to be resistant to pests and other pathogens common to *Verbena* plants.

It is claimed:

1. A new and distinct *Verbena* plant named 'WNVERSVCB24' as illustrated and described.

* * * * *